United States Patent [19]

Schirmann et al.

[11] 3,972,876

[45] Aug. 3, 1976

[54] PROCESS FOR THE PREPARATION OF SYMMETRICAL AND UNSYMMETRICAL AZINES AND MIXTURES THEREOF

[75] Inventors: Jean-Pierre Schirmann, Brignais; Francis Weiss, Pierre-Benite, both of France

[73] Assignee: Produits Chimiques Ugine Kuhlmann, Paris, France

[22] Filed: Dec. 13, 1974

[21] Appl. No.: 532,650

Related U.S. Application Data

[63] Continuation of Ser. No. 152,413, June 11, 1971, abandoned.

[30] Foreign Application Priority Data

June 12, 1970 France .............................. 70.21704
Feb. 24, 1971 France .............................. 71.06215
Dec. 29, 1970 France .............................. 70.46994
Mar. 3, 1971 France .............................. 71.07249

[52] U.S. Cl. .................. 260/240 G; 260/505 R; 260/505 E; 260/507 R; 260/508; 260/509; 260/510; 260/513 N; 260/514 S; 260/518 R; 260/518 A; 260/519; 260/534 R; 260/534 M; 260/558 A; 260/558 D; 260/559 A; 260/561 A; 260/566 B

[51] Int. Cl.² ...................................... C07C 109/00

[58] Field of Search ......... 260/566 B, 505 R, 505 E, 260/507 R. 508, 509, 510, 513 N, 514 S, 518 R, 518 A, 519, 534 R, 534 M, 558 A, 558 D, 559 A, 561 A

[56] References Cited
UNITED STATES PATENTS 2,870,206    1/1959    Meyer et al. ................... 260/566 B

*Primary Examiner*—Gerald A. Schwartz
*Attorney, Agent, or Firm*—Pennie & Edmonds

[57] ABSTRACT

A process is disclosed for the preparation of symmetrical azines of the formulas

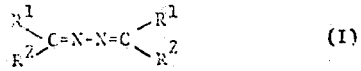

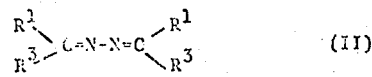

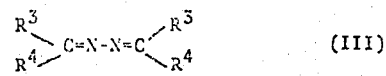

and unsymmetrical azines of the formulas

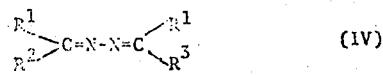

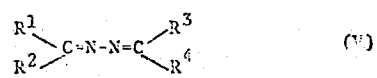

and mixtures of azines (I), (II), and (IV), and (I), (III) and (V), wherein $R^1$, $R^2$, $R^3$ and $R^4$ each is hydrogen, a straight-chain alkyl radical of from 1 to 12 carbon atoms, a branched-chain alkyl radical or a cycloalkyl radical of from 3 to 12 carbon atoms or a phenyl radical, the aforesaid radicals being unsubstituted or substituted with a radical which is stable in the medium in which said azines are produced; and in which case $R^1$ and $R^2$ can be the same or different radicals, $R^3$ is a radical different from $R^1$ and $R^2$, $R^3$ and $R^4$ are radicals different from each other, and each are different radicals from $R^1$ and $R^2$; or $R^1$ and $R^2$ or $R^1$ and $R^3$, or $R^3$ and $R^4$ of either or both the >C=N— moieties together form a cyclic or substituted cyclic radicals of from 3 to 11 carbon atoms in the ring.

18 Claims, No Drawings

PROCESS FOR THE PREPARATION OF SYMMETRICAL AND UNSYMMETRICAL AZINES AND MIXTURES THEREOF

This is a continuation of application Ser. No. 152,413 filed 6-11-71.

The process involves reacting a carbonyl compound of the formula

(VI)

alone or together with a different carbonyl compound

(VII)

or

(VIII)

wherein $R^1$, $R^2$, $R^3$ and $R^4$ each has the same meaning as defined above, with ammonia and hydrogen peroxide in the presence of a nitrile which is cyanogen or a nitrile of the formula

(IX)

wherein $n$ is an integer of from 1 to 6 and $R^5$ is a unsubstituted or substituted saturated aliphatic, acyclic or cyclic radical of from 1 to 12 carbon atoms or benzene or pyridine radical.

BACKGROUND OF THE INVENTION

I. Field of the Invention

This inventon relates to a process for the preparation of symmerical azines of the formulas

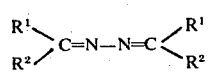

(I)

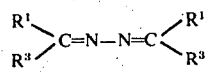

(II)

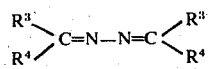

(III)

and unsymmetrical azines of the formulas

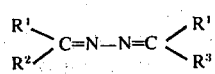

(IV)

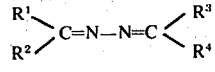

(V)

and mixtues of azines (I), (II) and (IV), and (I), (III) and (V), wherein $R^1$, $R^2$, $R^3$ and $R^4$ each has the same meaning as designated above.

II. Description of the Prior Art

Aldehydes are known to react with ammonia in a complex manner giving rise to various addition, condensation or polymerization products (see for example, *The Chemistry of the Carbon-Nitrogen Bond*, S. Patai. Interscience, London, 1967, page 67) and can react with hydrogen peroxide to form unstable peroxide products.

Moreover, it is known that ammonia, a ketone, and hydrogen peroxide react together to produce aminoperoxides (*J. Chem. Soc.* 1969, C, page 263) and in the presence of such catalysts as tungstic or molybdic acid, a amixture of cyclohexanone and ammonia is oxidized by hydrogen peroxide to form cyclohexanoneoxime (*J. Gen. Chem.* (U.S.S.R.) 1960, 30, 1635).

SUMMARY OF THE INVENTION

It has been surprisingly discovered that when at least one aldehyde or ketone or a mixture of at least one aldehyde and ketone is reacted with ammonia and hydrogen peroxide in the presence of a nitrile, a reaction takes place, the mechanism of which is not yet fully understood, which gives rise to an azine. When a single aldehyde is reacted, the resulting azine will be a symmetrical aldazine; when two or more aldehydes are reacted, the resulting mixture of azines will contain both symmetrical and unsymmetrical aldazines. When a single ketone is reacted, the resulting azine will be a symmetrical ketazine; when two or more ketones are reacted, the resulting mixture will contain both symmetrical and unsymmetrical ketazines. When the reaction mixture contains at least one aldehyde and ketone, in addition to yielding an aldazine and a ketazine the reaction will also produce an unsymmetrical azine possessing both aldazine and ketazine properties.

This invention relates to a process for the preparation of symmetrical azines of the formulas

(I)

(II)

(III)

and unsymmetrical azines of the formulas

(IV)

(V)

and mixtures of azines (I), (II) and (IV), and (I), (III) and (V), wherein $R^1$, $R^2$, $R^3$ and $R^4$ each is hydrogen, a straight chain alkyl radical of from 1 to 12 carbon atoms, a branched-chain alkyl radical or a cycloalkyl radical of from 3 to 12 carbon atoms or a phenyl radical, the aforesaid radicals being unsubstituted or substituted with a radical which is stable in the medium in which said azines are produced; and in which case $R^1$ and $R^2$ can be the same or different radicals, $R^3$ is a radical different from $R^1 R^2$, and $R^3$ and $R^4$ are radicals different from each other, and each are different radicals from $R^1$ and $R^2$; or $R^1$ and $R^2$, or $R^1$ and $R^3$, or $R^3$ and $R^4$ of either or both the >C=N— moieties together form cyclic or substituted cyclic radicals of from 3 to 11 carbon atoms in the ring.

The process involves reacting a carbonyl compound of the formula

  (VI)

alone or together with a different carbonyl compound

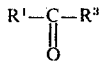  (VII)

or

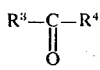  (VIII)

wherein $R^1$, $R^2$, $R^3$ and $R^4$ each has the same meaning as defined above, with ammonia and hydrogen peroxide in the presence of a nitrile which is cyanogen or a nitrile of the formula $$R^5(CN)_n \qquad (IX)$$

wherein $n$ is a integer of from 1 to 6 and $R^5$ is an unsubstituted or substituted saturated aliphatic, acyclic or cyclic radical of from 1 to 12 carbon atoms or benzene or pyridine radical.

When a single carbonyl compound (VI) is reacted according to the process of this invention, a symmetrical azine having the formula

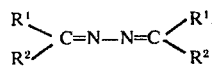  (I)

is produced.

When for example, both $R^1$ and $R^2$ of carbonyl compound (VI) is hydrogen, the carbonyl compound is formaldehyde and the azine resulting from this process is the symmetrical aldazine formaldazine which has the formula $$CH_2=N-N=CH_2$$

When only one of the substituents $R^1$ and $R^2$ is hydrogen, the resulting aldazine, for example, has the formula $$R^1-CH=N-N=CH-R^1$$

wherein the substituent $R^1$ is not hydrogen.

When neither of the substituents of the carbonyl compound (VI) is hydrogen, the carbonyl compound (VI) is a ketone and the resulting azine is a symmetrical ketazine of the formula

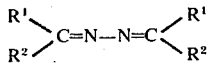  (I)

wherein none of the substituents $R^1$ and $R^2$ is hydrogen.

When in addition to carbonyl compound (VI), a different carbonyl compound (VII) is simultaneously reacted according to the process of this invention, a mixture of symmetrical and unsymmetrical azines of the formulas

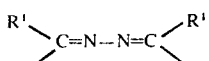  (II)

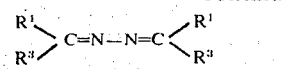  (II)

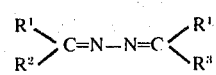  (IV)

is produced.

And if in addition to carbonyl compound (VI), a different carbonyl compound (VIII) is simultaneously reacted according to the process of this invention, a mixture of symmetrical and unsymmetrical azines of the formulas

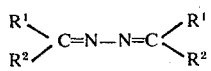  (I)

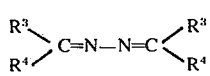  (I)

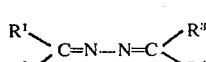  (IV)

is produced.

When both carbonyl compounds (VI) and (VII) or (VI) and (VIII) are aldehydes, a mixture of symmetrical and unsymmetrical aldazines will be obtained. Similarly, if both carbonyl compounds (VI) and (VII) or (VI) and (VIII) are ketones, a mixture of symmetrical and unsymmetrical ketazines will be produced. And if one of the carbonyl compounds (VI), (VII) or (VIII) is an aldehyde and the other carbonyl compound which is being simultaneously reacted is a ketone, the process of this invention will yield a mixture of azines containing a symmetrical aldazine, a symmetrical ketazine and a unsymmetrical azine possessing the characteristics of both an aldazine and a ketazine.

Any number of different aldehydes and/or ketones may be reacted according to the process of this invention to yield mixtures of azines the number of which are present in the mixture being made to depend upon the number of carbonyl compounds reacted.

DETAILED DESCRIPTION OF THE INVENTION

Some examples of aldehydes conforming to formulas (VI), (VII) or (VIII) which are advantageously employed in the process of this invention include formaldehyde, acetaldehyde, propionaldehyde, butyraldehyde, isobutyraldehyde, valeric aldehyde, pivalaldehyde, oenanthal, hexahydrobenzaldehyde, p-nitrobenzaldehyde and β-methoxypropionaldehyde.

Some examples of ketones conforming to formula (VI), (VII) or (VIII) which are advantageously employed in the process of this invention include acetone, 2-butanone, 2-pentanone, 3-pentanone, methylisopropylketone, methylisobutylketone, methylcyclohexylketone, acetophenone, benzophenone, cyclobutanone, cyclopentanone, cyclohexanone, 2-methylcyclohexanone, 4-methylcyclohexanone, 2,4-dimethyl cyclohexanone, 3,3,5-trimethylcyclohexanone, cycloheptanone, cyclooctanone, cyclodedanone and cyclododecanone.

The $R^1$, $R^2$, $R^3$ and $R^4$ radicals of the carbonyl compounds (VI), (VII), and (VIII) and the $R^5$ radical of the nitrile compounds (IX) which are useful in the process of this invention can be unsubstituted or substituted with one or several substituent groups advantageously selected from those groups which do not undergo any significant oxidation under the condition of the process, as for example, carbamyl, carboxylic, carboxylic ester, nitro, primary amine, secondary amine, tertiary amine, nitroso, fluoro, chloro, bromo, iodo, hydroxy, acetal, ether, epoxy, sulfoxide, sulfur, sulphone and sulphonic acid groups.

Some examples of nitriles conforming to formula (IX) which are advantageously employed in the process of this invention include, acetonitrile, propionitrile, butyronitrile, isobutyronitrile, cyclohexylcarboxylic nitrile, benzonitrile, ortho, meta or paratoluenenitrile, paramethoxybenzonitrile, metachlorobenzonitrile, paranitrobenzonitrile, mono, di and tri chloroacetonitrile, glycolonitrile, ε-hydroxycapronitrile, cyanoacetic acid and its alkyl esters, β-cyanopropionic acid and its alkyl esters, β-cyanopyridine, nicotinic nitrile, isonicotinic nitrile, acrylonitrile, methacrylonitrile, crotonitrile, Δ-3-tetrahydrobenzonitrile, 3,4-epoxy hexahydrobenzonitrile, β,β'-dicyanoethylsulphide, -sulphoxide or -sulphone, malononitrile, succinonitrile, glutaronitrile adiponitrile, pimelonitrile, suberonitrile, α-methyleneglutaronitrile, dihydromuconic nitriles, phthalonitriles, iminodiacetonitrile, nitrilotriacetonitrile and ethylenediaminetetracetinitrile.

A group of nitriles which has been found to be advantageous in carrying out this invention are obtained from cyanoethylation of numerous classes of compounds possessing reactive hydrogen atoms, with acrylonitrile or methylacrylonitrile. The substituted nitriles or polynitriles thus obtained are characterized by the presence at the β position thereof (with respect to the position of the nitrile function(s) of hydroxy, ether, carboxylic ester, amine or other groups, the precise group or groups present in the nitrile or polynitrile depending upon the nature of the active hydrogen compound(s) subjected to the cyanoethylation reaction. This category of substituted nitriles or polynitriles includes β-hydroxypropionitrile and β,β'-oxydipropionitrile which are obtained by the cyanoethylation of water, β-aminopropionitrile, β,β'-aminodipropionitrile and nitrilotripropionitrile which are obtained by the cyanoethylation of ammonia and the β-alkoxypropionitriles which are obtained by the cyanoethylation of alkanols. These nitriles may be partially formed in situ consuming the components of the reaction medium when acrylonitrile is used according to this invention, without impeding the reaction whereby the azines are formed. Other derivatives belonging to this category of nitriles include the cyanoethylation products of the polyols, for example, ethylene glycol, propylene glycol, glycerol and sorbitol, the carboxylic acids such as acetic acid, the hydroxyacids or hydroxy esters such as the alkyl ε-hydroxycaproates, and the primary or secondary alkylamines such as mono- and dimethylamine and mono- and diethylamine.

The use of a nitrile possessing another reactive group in its molecule can involve a reaction of this group during the process as has been previously pointed out with the acrylic nitriles which can cyanoethylate various components of the reaction medium. For example, the double bonds of an unsaturated nitrile can undergo epoxydation and tertiary amine groups can be oxidized to form aminoxide groups thus consuming a portion of the hydrogen peroxide present in the reaction medium. It is advantageous in this case simply to adjust the amount of hydrogen peroxide in the reactor in a manner which is evident to one skilled in the art.

An advantageous method for preparing the azines according to this invention comprises reacting the components of the reaction medium in an aqueous solution or in the presence of a solvent. The solvent is advantageously selected from among the mono alkanols having from one to four carbon atoms, for example, methanol, ethanol, n-propanol, isopropanol, n-butanol, sec-butanol and isobutanol. The reaction temperature is advantageously between about 0° and about 100°C. The reaction can be carried out at about atmospheric pressure or at a pressure of up to about ten atmospheres if pressure is necessary to maintain the ammonia in the reaction medium.

The reactants can be employed in stoichiometric amounts but a molar lack or excess of one or several reagents can also be utilized. For example, from about 0.2 to about 5 moles of aldehyde or ketone or combined aldehyde(s) and/or ketone(s) and ammonia per mole of hydrogen peroxide can be employed. The quantity of nitrile which is advantageously employed in this process can vary from about 1 to about 10 equivalents of nitrile per mole of hydrogen peroxide.

The reactants can be used in their commercially available form. For example, hydrogen peroxide can be used in aqueous solutions of 30–90% hydrogen peroxide by weight and ammonia can be used either in anhydrous form or in the usual aqueous solution.

The reactants can be introduced into the reactor either simultaneously or in random sequence at a rate which will permit effective control of the exothermic reaction. The carbonyl compounds of this invention can be reacted with hydrogen peroxide in the known manner and the resulting peroxides can then be reacted with ammonia in the presence of a nitrile. Similarly, the carbonyl compounds of this invention can be reacted with ammonia before adding the hydrogen peroxide and nitrile. And finally, an aminoperoxide can be prepared in the known manner by the reaction of a carbonyl compound, ammonia and hydrogen peroxide and this aminoperoxide can then be reacted with a nitrile to yield an azine.

It is advantageous to add a stabilizing agent for hydrogen peroxide to the reaction medium such as phosphoric acid, nitrilotriacetic acid, ethylenediaminotetraacetic acid, the sodium salts of the aforesaid acids, and as a catalyst, an effective amount of an ammonium salt or an alkaline metal salt, for example, a lithium, sodium or potassium salt of a mineral hydracid or oxyacid, or of an aliphatic or aromatic carboxylic acid or arylsulphonic acid having less than 20 carbon atoms, the anions of which are stable under the oxidizing conditions of the reaction medium.

Some of the useful ammonium salts or alkaline metal salts include the ammonium lithium, sodium and potassium salts whose anion is a fluoride, chloride, sulphate, nitrate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulphonate, ethanesulphonate, benzenesulphonate and p-toluenesuphonate. The quantity of salt used can vary from 0.01 to 2% by weight of the total reaction mixture. The salt can be formed in situ. For example, if it is desired to employ an ammonium salt, the salt may be formed in situ by adding an acid to the ammonia-containing reaction medium.

Azines are very useful as intermediate products for a variety of syntheses, particularly in the manufacture of hydrazine and numerous organic nitrogen compounds employed as pesticides or as pharmaceutical products. In the manufacture of hydrazine, for example, azines can be reacted with water and/or a strong acid to produce hydrazine hydrate and/or a hydrazine salt. The hydrazine hydrate and/or hydrazine salt are readily converted to hydrazine employing well known processes.

The chemical titration of the azines prepared according to the following examples was performed either by gas phase chromatography or chemical analysis.

The chemical titration of the azines present in the reaction medium was carried out by iodometry upon a sample in which he non-consumed hydrogen peroxide was previously titrated. According to this procedure, a quantity of reaction mixture containing about 2 milliequivalents of hydrogen peroxide was withdrawn from the reactor, weighed, and 12 cm³ of aqueous sulphuric acid (30% by weight) followed by 12 cm³ of aqueous potassium iodide (30% by weight) were added to the mixture. After standing for 15 minutes in darkness, the released iodine was titrated by a decinormal solution of sodium thiosulphate.

During this quantitative determination of the amount of hydrogen peroxide in the highly acidic reaction medium, the azine present in the medium hydrolyzed to hydrazine sulphate which does not reduce iodine under acid conditions. 50 cm³ of a decinormal aqueous solution of iodine followed by 30 g of crystallized sodium acetate was added to the sample in order to adjust the pH to about 5. The sample was stirred and a release of nitrogen was observed which ceased after about two minutes. The nitrogen given off by the sample resulted from the reduction of the hydrazine according to the reaction

$N_2H_4 + 2I_2 \rightarrow N_2 + 4HI$

Thereafter, the excess iodine was titrated by a decinormal solution of sodium thiosulfate.

Examples 1 through 43 demonstrate the process of this invention for the production of symmetrical aldazines and ketazines conforming to formula (I). By utilizing the same procedures as disclosed in the Examples except that two or more different aldehydes or ketones or one or more aldehyde and ketone is reacted, a mixture of symmetrical and unsymmetrical azines will result as hereinbefore described.

EXAMPLE 1

A solution of 103 g of benzonitrile (1 mole), 18 g of water, 1 g of the disodium salt of ethylenediaminotetracetic acid and 0.15 g of ammonium acetate and 320 g of methanol were placed in a reaction vessel. 23 g (1.35 mole) of gaseous ammonia were bubbled through the reaction mixture dissolving therein. Then, 72 g of isobutyraldehyde (1 mole) and separately, 28 g of a 61% aqueous solution hydrogen peroxide (0.5 mole) were progressively introduced into the medium at 25°C. The mixture was left to react for 48 hours at the same temperature. At the end of the reaction, the mixture was titrated. The quantity of isobutyraldazing determined by chemical analysis was 23 g (0.163 mole).

The methanol and the untransformed isobutyraldehyde were then evaporated under 200 mm Hg pressure. The benzamide which crystallized was filtered, and the filtrate was extracted with chloroform. The chloroform extract was dried over anhydrous sodium sulphate, evaporated, and the isobutyraldazine was distilled under 200 mm Hg pressure: 11.7 g of isobutyraldazine boiling at 66°C under 20 mm Hg were thus obtained.

The product obtained was identified by its mass and infrared spectra (band C = N— at 1660 cm⁻¹) compared with the product synthesized by reaction of isobutyraldehyde with hydrazine hydrate.

EXAMPLE 2

The same procedure employed in EXAMPLE 1 was repeated, except that benzonitrile was replaced by 41 g of acetonitrile (1 mole). After reacting for 48 hours at 25°C, the mixture titrated 9.8 g of isobutyraldazine (0.07 mole).

EXAMPLE 3

A solution of 51.5 g of benzonitrile (0.5 mole), 18 g of water, 0.5 of the disodium salt of ethylenediaminetetracetic acid, 0.05 g of acetic acid and 160 g of methanol were placed in a reaction vessel. 8.5 g of gaseous ammonia (0.5 mole) were bubbled into the mixture dissolving therein. 29 g of propionaldehyde (0.5 mole), followed by 14 g of a 61% aqueous solution of hydrogen peroxide (0.25 mole) were then added. The mixture was left to react for 24 hours at 25°C, after which 6.7 g of propionaldazine (0.06 mole) were titrated in the mixture. A recovery procedure identical to the one employed in EXAMPLE 1, resulted in the isolation of 3.4 g of pure propionaldazine boiling at 45°C under 20 mm Hg, the infrared spectrum (band C = N— at 1660 cm⁻¹) of which was identical to that of the product prepared from propionaldehyde and hydrazine hydrate.

EXAMPLE 4

EXAMPLE 3 was repeated, except that propionaldehyde was replaced by 53 g of benzaldehyde (0.5 mole). After 24 hours at 25°, 14.6 g of benzaldazine (0.07 mole) were titrated in the mixture. The usual recovery procedure resulted in the isolation of 8 g of pure benzaldazine, in the form of yellow crystals, having a melting point of 92°C, the infrared spectrum of which (band C = N— at 1625 cm⁻¹) was identical to the spectrum reported by the literature (Anal. Chem. 36, 1349 (1964).

EXAMPLE 5

20.5 g of acetonitrile (0.5 mole) were added to 160 g of methanol and the mixture was heated to 40°C. Then simultaneously over 1 hour, 24.3 g of a 70% by weight solution of hydrogen peroxide (0.5 mole H₂O₂) and a mixture of 49 g of cyclohexanone, 45 g of an 18.8% by weight solution of ammonia (0.5 mole) 16 g methanol and 0.5 g of the disodium salt of ethylenediaminetetraacetic acid (EDTA) were added to the acetonitrile/methanol mixture. Residence time in the reaction vessel was three hours after which quantitative analysis by gas phase chromatography indicated the presence of 33.5 g cyclohexanone azine (0.175 mole) which corresponds to a yield of 35% based on hydrogen peroxide, The reaction solution was then evaporated under 200 mm Hg until the temperature reached 50°C. The residue was extracted with chloroform and the resulting extract was dried over anhydrous sodium sulfate and distilled. Thus 29.4 g of pure cyclohexanone azine (0.153 mole) boiling at 87°–88°C under 0.2 mm Hg was recovered and crystallized upon cooling at 37°C. This product has the identical spectrum to the one reported in the literature (An. Chem. 1964, 36 (7), 1349) (characteristic band C = N— at 1640 cm$^{-1}$). Its ultraviolet spectrum measured upon a solution of the product in cyclohexanone indicated a λ max. of 216 mμ with absorption at 234 mμ and its nuclear magnetic resonance spectrum in CD Cl$_3$ at 60 megahertz indicated two groups of peaks centered at δ = 1.60 and 2.38 ppm with an intensity ratio of 3/2.

EXAMPLE 6

73.5 g of cyclohexanone (0.75 mole), 77.2 g of benzonitrile (0.75 mole) and 240 g of methanol were mixed together. This mixture was saturated at 25°C with ammonia which was bubbled into the mixture. 21 g of ammonia (1.25 mole) were thus absorbed. Then, over one hour at 25°C, 36.5 g of a 70% solution of hydrogen peroxide (0.75 mole) were added. Thereafter the mixture was left to react for 2 hours and a quantity of cyclohexanone-azine was formed which corresponds to a yield of 34.4% based on the hydrogen peroxide.

EXAMPLE 7

51.5 g of benzonitrile (0.5 mole), 160 g of methanol and 0.5 g of tetracetic ethylenediamine acid were mixed together. This mixture was brought to 40°C, and then there was simultaneously added to it over one hour, 24.3 g of a 70% solution of hydrogen peroxide (0.5 mole) and a mixture of 49 g of cyclohexanone (0.5 mole), 45 g of an 18.8% by weight solution of ammonia (0.5 mole) and 25 g of methanol. Thereafter, the mixture was left to react for two and a half hours after which the quantity of cyclohexanoneazine present in the medium after was measured by gas phase chromatography. 25.5 g of cyclohexanone-azine (0.133 mole) were formed, which corresponds to a yield of 26% based on hydrogen peroxide.

EXAMPLE 8

240 g of methanol, 77.3 g of benzonitrile (0.75 mole), 43.5 g of acetone (0.75 mole) and 55.5 g of a 23% by weight solution of ammonia (0.75 mole) were mixed together and then heated to 40°. 36.5 g of an aqueous solution by weight of 70% hydrogen peroxide (0.75 mole) were added to this mixture over one hour. The mixture was maintained at 40°C and after three hours, the quantity of acetone-azine which was present in the medium was determined by gas phase chromatography. 16.5 g of acetone-azine (0.148 mole) was formed, which corresponds to a yield of 19.8% based on hydrogen peroxide.

EXAMPLE 9

20.5 g of acetonitrile (0.5 mole), 90 g of an 18.8% by weight solution of ammonia (1 mole), 72 g of methylethylketone (1 mole) and 160 g of methanol were mixed together. Then over one hour at the room temperature, 24.3 g of a 70% solution of hydrogen peroxide (0.5 mole) were added. After two hours of reaction, the quantity of methylethylketoneazine which was present in the medium was determined by gas phase chromatograph. 12 g of methylethylketoneazine (0.085 mole) were formed which corresponds to a yield of 17% based on hydrogen peroxide.

EXAMPLE 10

20.5 g of acetonitrile (0.5 mole), 90 g of an 18.8% solution of ammonia (1 mole), 86 g of 2-pentanone (1 mole) and 160 g of methanol were mixed together. Then, over one hour at the room temperature, 24.3 g of a 70% solution of hydrogen peroxide (0.5 mole) were added. After two hours of reaction, the quantity of pentanone-2-azine which was present in the medium was determined by gas phase chromatography. 8.7 g of pentanone-2-azine (0.052 mole) were formed.

EXAMPLE 11

A solution of 20.5 g (0.5 mole) of acetonitrile, 58 g (1 mole) of acetone, 18 g (1 mole) of water, 1 g of the disodium salt of ethylenediaminetetracetic acid and 0.15 g of ammonium acetate in 160 g of methanol (5 moles) were put in a reaction vessel and then gaseous ammonia was bubbled into the reaction medium until 14.6 g (0.86 mole) of this reagent were dissolved in the medium. The mixture was brought to 50°C and within 5 minutes, 19.5 g of a 70% solution of hydrogen peroxide (0.4 mole) were added. The medium was left to react for 7 hours at the same temperature while bubbling gaseous ammonia into the medium at the rate of 1.7 g (0.1 mole) per hour. At the end of the reaction period, the mixture was titrated. The quantity of acetone-azine determined by chemical analysis and by gas phase chromatography was 35.3 g (0.315 mole) which corresponds to a yield of 78.5% based on hydrogen peroxide.

EXAMPLE 12

EXAMPLE 11 was repeated exactly, except ammonium acetate was replaced by 0.09 g of acetic acid, in order to produce ammonium acetate in situ. After seven and a half hours of reaction, 36 g (0.32 mole) of acetone-azine were titrated in the mixture, which corresponds to a yield of 80% based on hydrogen peroxide.

EXAMPLES 13 to 24

EXAMPLE 11 was repeated exactly, except that ammonium acetate was successively replaced by various salts. EXAMPLE 24 had been carried out in the absence of an additional salt to serve as a comparative test. The experimental results obtained are reported in the following table:

TABLE 1

| EXAMPLE | COMPOSITION OF THE SALT | QUANTITY g. | YIELD OF ACETONE-AZINE BASED ON H$_2$O$_2$ (mole %) |
|---|---|---|---|
| 13 | Ammonium chloride | 0.107 | 70 |
| 14 | Ammonium sulphate | 0.264 | 69.5 |
| 15 | Ammonium nitrate | 0.160 | 71.5 |
| 16 | Ammonium carbonate | 0.228 | 75 |
| 17 | Borax (Na$_2$ B$_4$ O$_7$.10 H$_2$O) | 0.762 | 77 |
| 18 | Monosodium phosphate | 0.100 | 65 |
| 19 | Ammonium formiate | 0.126 | 69 |
| 20 | Ammonium oxalate | 0.284 | 65 |

TABLE 1-continued

| EXAMPLE | COMPOSITION OF THE SALT | QUANTITY g. | YIELD OF ACETONE-AZINE BASED ON $H_2O_2$ (mole %) |
|---|---|---|---|
| 21 | Ammonium n-octanoate | 0.322 | 69 |
| 22 | Ammonium benzoate | 0.288 | 55 |
| 23 | Lithium carbonate | 0.148 | 55 |
| 24 | | 0 | 51 |

EXAMPLE 25

184 g (1 mole) of cyclododecanone, 20.5 g (0.5 mole of acetonitrile, 18 g of water (1 mole), 0.1 g of the disodium salt of ethylenediaminetetracetic acid and 0.1 g of acetic acid were dissolved in 480 g of methanol. Anhydrous ammonia was bubbled into the reaction medium causing 17 g (1 mole) of this reagent to become dissolved therein. The medium was heated to 50°C and there was introduced into the medium over 5 minutes, 20 g of a 70% solution of hydrogen peroxide (0.4 mole). After reacting for 2 hours, 18 g (0.05 mole) of cyclododecanoneazine were titrated in the mixture which corresponds to a yield of 12.5% based on hydrogen peroxide.

EXAMPLE 26

120 g (1 mole) of acetophenone, 20.5 g (0.5 mole) of acetonitrile, 18 g of water (1 mole), 1 g of the disodium salt of ethylenediaminetetracetic acid and 0.15 g of ammonium acetate were dissolved in 160 g of methanol. Gaseous ammonia was bubbled into the medium causing 16.7 g (0.984 mole) of this reactant to become absorbed therein. The medium was heated at 50°C and within 5 minutes, 21.5 g of a 70% solution of hydrogen peroxide (0.44 mole) were added. After reacting for 1 hour, 23 g (0.1 mole) of acetophenone-azine were titrated in the mixture which corresponds to a yield of 22.8% based on hydrogen peroxide.

EXAMPLE 27

A solution comprising 20.5 g of acetonitrile (0.5 mole) 58 g of acetone (1 mole), 18 g of water, 1 g of the disodium salt of ethylenediaminetetracetic acid and 0.2 g of ammonium acetate were placed into a reaction vessel. The mixture was raised to 50°C and 2.3 g of ammonia (0.135 mole) were dissolved therein by being bubbled through the medium. Then, 20.5 g of a 67% solution of hydrogen peroxide (0.40 mole) were introduced into the medium over two hours while continuously bubbling ammonia gas therein at a rate of 2.6 g/hour (0.15 mole/hour). The medium was left to react for 7 hours at the same temperature. At the end of the reaction, the mixture was titrated. The quantity of acetoneazine determined by chemical anlaysis and gaseous chromatography was 31.4 g (0.28 mole) which corresponded to a yield of 70% based on hydrogen peroxide.

EXAMPLE 28

20.5 g of acetonitrile (0.5 mole), 58 g of acetone (1 mole) and 160 g of methanol were introduced into a one liter stainless steel autoclave, along with a solution of 1.2 g of the disodium salt of ehtylenediaminetetracetic acid and 0.2 g of ammonium acetate in 18 g of water. Then, 15 g of ammonia (0.88 mole) and 20.6 g of a 64.5% solution of hydrogen peroxide (0.39 mole) were introduced into the reaction medium. The autoclave was closed and heated at 70°C for 2 hours under 3 bars autogenous pressure. At the end of the reaction, 30.7 g (0.274 mole) of acetoneazine present were titrated in the mixture, corresponding to a yield of 70% based on hydrogen peroxide.

EXAMPLE 29

A solution of 42.5 g of β-methoxypropionitrile (0.5 mole), 58 g of acetone (1 mole), 18 g of water, 1 g of the disodium salt of ethylenediaminetetracetic acid and 0.1 g of acetic acid and 160 g of methanol were placed in a reaction vessel. The medium was heated at 50°C and 15.8 g of ammonia (0.93 mole) were dissolved by being bubbled into the reaction mixture. Then 20.1 g of a 70% solution of hydrogen peroxide (0.4 mole) were added. The reaction medium was left to react for 7 hours during which gaseous ammonia was bubbled therein at a rate of 1.7 g/hour. At the end of the reaction period, the usual titration indicated that the mixture contained 36 g of acetoneazine (0.32 mole) which corresponded to a yield of 80% based on hydrogen peroxide.

EXAMPLE 30

EXAMPLE 29 was repeated exactly, except that β-methoxypropionitrile was replaced by 34.5 g of n-butyronitrile (0.5 mole). A mixture containing 23.5 g of acetoneazine (0.21 mole) was obtained with a yield of 53% based on hydrogen peroxide.

EXAMPLE 31

EXAMPLE 29 was repeated exactly, except that β-methoxypropionitrile was replaced by 42.5 g of cyanoacetic acid (0.5 mole). After reacting for 3 hours, a mixture containing 11.7 g of acetoneazine (0.105 mole) was obtained, with a yield of 26% based on hydrogen peroxide.

EXAMPLE 32

EXAMPLE 29 was repeated exactly, except that β-methoxypropionitrile was replaced by 100 g of methyl-9-cyano-7-oxanonanoat (0.5 mole). After reacting for 3 hours, a mixture containing 14 g of acetoneazine (0.125 mole) was obtained with a yield of 31% based on hydrogen peroxide.

EXAMPLE 33

EXAMPLE 29 was repeated exactly, except that β-methoxypropionitrile was replaced by 35 g of β-aminopropionitrile (0.5 mole). A mixture containing 9.4 g of acetoneazine (0.084 mole) was obtained with a yield of 21% based on hydrogen peroxide.

EXAMPLE 34

EXAMPLE 29 was repeated exactly, except that β-methoxypropionitrile was replaced by 24 g of iminodiacetonitrile (0.25 mole, i.e. 0.5 nitrile equivalent). After reacting for 5 hours, a mixture containing 27 g of acetoneazine (0.24 mole) was obtained, with a yield of 60% based on hydrogen peroxide.

EXAMPLE 35

EXAMPLE 29 was repeated exactly, except that β-methoxypropionitrile was replaced by 35.5 g of β-hydroxypropionitrile (0.5 mole). A mixture containing 33 g of acetoneazine (0.295 mole) was obtained which corresponded to a yield of 74% based on hydrogen peroxide.

EXAMPLE 36

EXAMPLE 29 was repeated exactly, except that β-methoxypropionitrile was replaced by 33.5 g of methacrylonitrile (0.5 mole). A mixture containing 28 g of acetoneazine (0.25 mole) was obtained which corresponded to a yield of 62.5% based on hydrogen peroxide.

EXAMPLE 37

EXAMPLE 29 was repeated exactly, except that β-methoxypropionitrile was replaced by 52 g of nicotinic nitrile (0.5 mole). A mixture containing 30 g of acetoneazine (0.27 mole) was obtained which corresponded to a yield of 67% based on hydrogen peroxide.

EXAMPLE 38

EXAMPLE 29 was repeated exactly, except that β-methoxypropionitrile was replaced by 45 g of β-chloro propionitrile (0.5 mole). A mixture containing 29.5 g of acetoneazine (0.26 mole) was obtained which corresponded to a yield of 65% based on hydrogen peroxide.

EXAMPLE 39

A solution of 12.5 g of succinonitrile (0.155 mole, i.e., 0.31 nitrile equivalent), 35 g of acetone (0.62 mole), 11.25 g of water, 0.625 g of the disodium salt of ethylenediaminetetracetic acid and 0.1 g of ammonium acetate were placed in a reaction vessel containing 100 g of methanol. The medium was heated to 40°C and 10.6 g of ammonia (0.625 mole) were dissolved therein by bubbling. Then, 12.15 g of a 70% solution of hydrogen peroxide (0.25 mole) were introduced into the medium over 2 hours. The mixture was then maintained for 3 hours at 40°C, with a light flow of ammonia being bubbled into the medium. At the end of the reaction, the mixture was titrated as usual. 18 g of acetoneazine (0.16 mole) had formed, which corresponded to a yield of 64% on the basis of hydrogen peroxide.

EXAMPLE 40

EXAMPLE 39 was repeated exactly, except that succinonitrile was replaced by 14.65 g of glutaronitrile (0.155 mole). After a total reaction time of 6 hours (including time required for adding reaction components), 15.7 g of acetoneazine (0.14 mole) had formed which corresponded to a yield of 56% based on hydrogen peroxide.

EXAMPLE 41

EXAMPLE 39 was repeated exactly, except that succinonitrile was replaced by 16.7 g of adiponitrile (0.155 mole) and the temperature was raised to 50°. After a total reaction duration of 7 hours, 14.5 g of acetoneazine (0.13 mole) had formed, which corresponded to a yield of 52% on the basis of hydrogen peroxide.

EXAMPLE 42

EXAMPLE 39 was repeated exactly, except that 19.2 g of β,β-oxydipropionitrile (0.155 mole) were employed. 16.2 g of acetoneazine (0.145 mole) had formed which corresponded to a yield of 58% based on hydrogen peroxide.

EXAMPLE 43

19.4 g of ethylene diaminetetracetonitrile (0.09 mole, i.e. 0.36 nitrile equivalent), 41.2 g of acetone (0.71 mole), 117 g of methanol, 13.2 g of water and 0.15 g of ammonium acetate were placed in a reaction vessel. The medium was heated to 50°C and 13.6 g of ammonia (0.8 mole) were dissolved therein by bubbling. 15.4 g of a 66.8% hydrogen peroxide (0.3 mole) were then introduced into the medium over half an hour. The mixture was maintained at 50°C for 3 hours while bubbling ammonia therein at a rate of about 3 g/hour. At the end of the reaction, the mixture was titrated as usual. 16 g of acetoneazine (0.143 mole) had formed, which corresponded to a yield of 48% on the basis of hydrogen peroxide.

We claim:
1. The process for the preparation of symmetrical azines of the formulas

and unsymmetrical azines of the formulas

and mixtures of azines (I), (II) and (IV), and (I), (III) and (V), wherein $R^1$, $R^2$, $R^3$ and $R^4$ each is hydrogen, a straight-chain alkyl radical of from 1 to 12 carbon atoms, a branched-chain alkyl radical or a cycloalkyl radical of from 3 to 12 carbon atoms or a phenyl radical, the aforesaid radicals being unsubstituted or substituted with one or more halogen atoms or carbamyl, carboxylic, nitro, amino, nitroso, hydroxy, methoxy or sulphonic acid groups; and in which case $R^1$ and $R^2$ can be the same or different radicals, $R^3$ is a radical different from $R^1$ and $R^2$, $R^3$ and $R^4$ are radicals different from each other, and each are different radicals from $R^1$ and $R^2$; or $R^1$ and $R^2$, or $R^1$ and $R^3$, or $R^3$ and $R^4$ of either or both the >C=N— moieties together form an alkylene radical of from 3 to 11 carbon atoms, said alkylene radical being unsubstituted or substituted by one or more of the above atoms or groups, which comprises reacting a carbonyl compound of the formula

alone or together with a different carbonyl compound

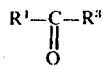
(VII)

or

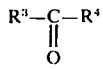
(VIII)

wherein $R^1$, $R^2$, $R^3$ and $R^4$ each has the same meaning as defined above, with ammonia and hydrogen peroxide in the presence of cyanogen or a nitrile of the formula

(IX)

wherein $n$ is a integer of from 1 to 6 and $R^5$ is a saturated aliphatic or alicyclic radical of from 1 to 12 carbon atoms or a benzene or pyridine radical, the aforesaid radical being unsubstituted or substituted with one or more of the above atoms or groups.

2. A process for the preparation of azines which comprises reacting ammonia, hydrogen peroxide and a carbonyl compound selected from formaldehyde, acetaldehyde, propionaldehyde, butyraldehyde, isobutyraldehyde, valeric aldehyde, pivalaldehyde, oenanthal, hexahydrobenzaldehyde, p-nitrobenzaldehyde, β-methoxypropionaldehyde, acetone, 2-butanone, 2-pentanone, 3-pentanone, methylisopropylketone, methylisobutylketone, methylcyclohexylketone, acetophenone, benzophenone, cyclobutanone, cyclopentanone, cyclohexanone, 2-methylcyclohexanone, 4-methylcyclohexanone, 2,4-dimethylcyclohexanone, 3,3,5-trimethylcyclohexanone, cycloheptanone, cyclooctanone, cyclodecanone and cyclododecanone, and mixtures thereof, in the presence of cyanogen or a nitrile selected from acetonitrile, propionitrile, butyronitrile, isobutyronitrile, cyclohexylcarboxylic nitrile, benzonitrile, a toluenenitrile, paramethoxybenzonitrile, metachlorobenzonitrile, paranitrobenzonitrile, mono, di and tri chloroacetonitrile, glycolonitrile, ε-hydroxycapronitrile, cyanoacetic acid and its alkyl esters, β-cyanopropionic acid and its alkyl esters, β-cyanopyridine, nicotinic nitrile, isonicotonic nitrile, acrylonitrile, methacrylonitrile, crotonitrile, Δ-3-tetrahydrobenzonitrile, 3,4-epoxyhexahydrobenzonitrile, β,β'-dicyanoethylsulphide, -sulphoxide and -sulphone, malononitrile, succiononitrile, glutaronitrile, adiponitrile, pimelonitrile, suberonitrile, α-methyleneglutaronitrile, a dihydromuconic nitrile, a phthalonitrile, iminodiacetonitrile, nitrilotriacetonitrile, ethylenediametetracetonitrile, β-hydroxypropionitrile, β,β'-oxydipropionitrile, β-aminopropionitrile, β,β'-iminodipropionitrile, nitrilotripropionitrile, β-alkoxypropionitriles and nitriles obtained by cyanoethylation with acrylonitrile or methylacrylonitrile of ethylene glycol, propylene glycol, glycerol, sorbitol, acetic acid, alkyl ε-hydroxycaproates, mono- and dimethylamine, and mono- and diethylamine.

3. The process of claim 1 wherein one aldehyde conforming to the formula of carbonyl compound (VI) is reacted.

4. The process of claim 2 wherein the aldehyde is formaldehyde, acetaldehyde, propionaldehyde, butyraldehyde, isobutyraldehyde, valerylaldehyde, pivaldehyde, oenanthal, hexahydrobenzaldehyde, p-nitrobenzaldehyde, or β-methoxypropionaldehyde.

5. The process of claim 1 wherein one ketone conforming to the formula of carbonyl compound (VI) is reacted.

6. The process of claim 4 wherein the ketone is acetone, 2-butanone, 2-pentanone, 3-pentanone, methylisopropylketone, methylisobutylketone, methycyclohexylketone, acetophenone, benzophenone, cyclobutanone, cyclopentanone, cyclohexanone, 2-methylcyclohexanone, 4-methylcyclohexanone, 2,4-dimethylcyclohexanone, 3,3,5-trimethylcyclohexanone, cycloheptanone, cyclooctanone, cyclodecanone or cyclododecanone.

7. The process of claim 1 wherein the carbonyl compound (VI) is reacted together with the different carbonyl compound (VII) or (VIII).

8. The process of claim 7 wherein both carbonyl compounds (VI) and (VII) or (VI) and (VIII) are aldehydes.

9. The process of claim 7 wherein both carbonyl compounds (VI) and (VII) or (VI) and (VIII) are ketones.

10. The process of claim 7 wherein the carbonyl compound (VI) is an aldehyde and the carbonyl compound (VII) or (VIII) is a ketone.

11. The process of claim 1 wherein the nitrile is obtained by cyanoethylation of active-hydrogen compounds with acrylonitrile or methacrylonitrile.

12. The process of claim 11 wherein the active-hydrogen compound is water, ammonia, an alkanol, polyol, carboxylic acid, hydroxyacid, hydroxyester, or primary or secondary alkylaminated compound.

13. The process of claim 1 wherein the nitrile is acetonitrile, propionitrile, butyronitrile, isobutyronitrile, cyclohexylcarboxylic nitrile, benzonitrile, ortho, meta or paratoluenenitrile, paramethoxybenzonitrile, metachlorobenzonitrile, paranitrobenzonitrile, mono, di and tri chloroacetonitrile, glycolonitrile, ε-hydroxycapronitrile, cyanoacetic acid and its alkyl esters, β-cyanopropionic acid and its alkyl esters, β-cyanopyridine, nicotinic nitrile, isonicotinic nitrile, acrylonitrile, methacrylonitrile, crotonitrile, Δ-3 tetrahydrobenzonitrile, 3,4-epoxyhexahydrobenzonitrile, β,β'-dicyanoethylsulphide, -sulphoxide or -sulphone, malononitrile, succinonitrile, glutaronitrile, adiponitrile, pimelonitrile, suberonitrile, a-methyleneglutaronitrile, dihydromuconic nitriles, phthalonitriles, iminodiacetonitrile, nitrilotriacetonitrile or ethylenediaminetetracetonitrile.

14. The process of claim 1 wherein the nitrile is added to the reaction medium.

15. The process of claim 1 wherein the nitrile is formed in situ within the reaction medium.

16. The process of claim 1 wherein from about 0.2 to about 5 moles of carbonyl compound and ammonia per mole of hydrogen peroxide are reacted.

17. The process of claim 16 wherein from about 1 to about 10 molar equivalents of nitrile per mole of hydrogen peroxide are present in the reaction mixture.

18. The process of claim 1 wherein a catalyst is added which catalyst is an ammonium salt or an alkaline metal salt of an aliphatic or aromatic carboxylic acid or arylsulphonic acid having less than 20 carbon atoms, the anion of which is a halogen atom or a sulphate, nitrate, phosphate, pyrophosphate, borate, carbonate, formate, acetate, propionate, butyrate, isobutyrate, hexanoate, octanoate, dodecanoate, stearate, oxalate, succinate, glutarate, adipate, benzoate, phthalate, methanesulphonate, ethanesulphonate, benzenesulphonate, or p-toluenesulphonate group.

* * * * *

UNITED STATES PATENT AND TRADEMARK OFFICE
CERTIFICATE OF CORRECTION

PATENT NO. : 3,972,876
DATED : August 3, 1976
INVENTOR(S) : Jean-Pierre Schirmann et al.

It is certified that error appears in the above-identified patent and that said Letters Patent are hereby corrected as shown below:

Column 2, line 8 "a amixture" should be --a mixture--

Column 4, line 66 "cyclodedanone" should be --cyclodecanone--

Column 7, line 16 "which he" should be --which the--

Column 7, line 39 "$N_2H_4 + 2I_2 \quad N_2 + 4HI$" should be --

$$N_2H_4 + 2I_2 \rightarrow N_2 + 4HI$$ --

Column 7, line 64 "isobutyraldazing" should be -- isobutyraldazine--

Column 11, line 64 - 65 "ehtylenediaminetetracetic" should be --ethylenediaminetetracetic--

Signed and Sealed this

Thirtieth Day of November 1976

[SEAL]

Attest:

RUTH C. MASON
*Attesting Officer*

C. MARSHALL DANN
*Commissioner of Patents and Trademarks*